Figure 1:
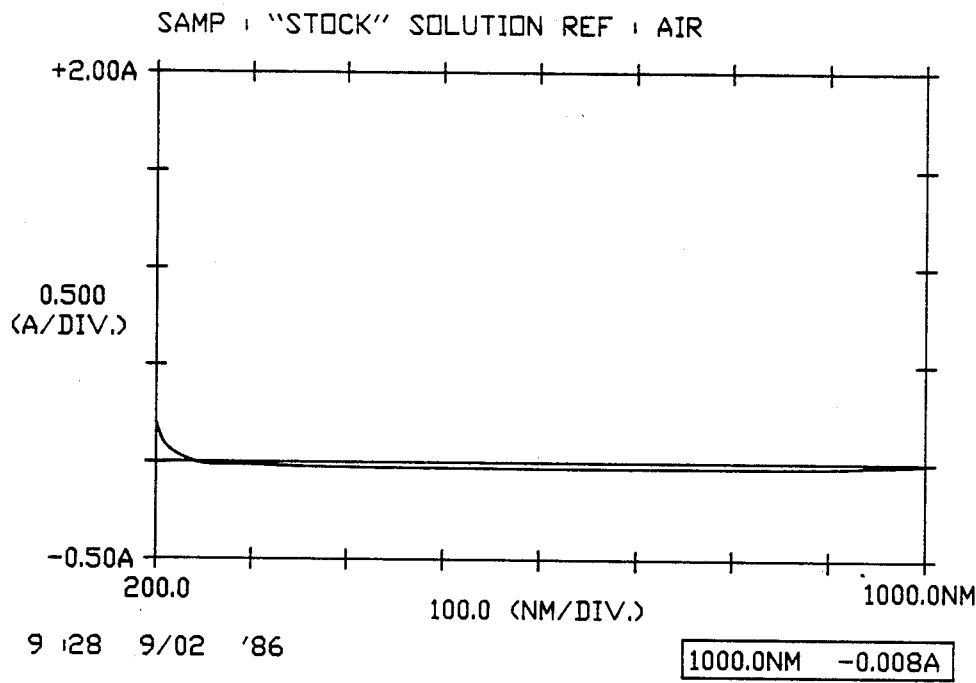

United States Patent [19]

Allen

[11] Patent Number: 4,853,374
[45] Date of Patent: Aug. 1, 1989

[54] VISCOELASTIC VITREOUS SUBSTITUTE WITH UV BLOCKER

[75] Inventor: Mark D. Allen, Lakewood, Colo.

[73] Assignee: M.D.R. Group, Inc., Denver, Colo.

[21] Appl. No.: 60,013

[22] Filed: Jun. 9, 1987

[51] Int. Cl.$^4$ .............................................. A61K 31/72
[52] U.S. Cl. ..................................... 514/57; 351/162; 351/163
[58] Field of Search ................... 514/57; 8/507, 549, 8/543; 351/162, 163

[56] References Cited

U.S. PATENT DOCUMENTS

| | | | |
|---|---|---|---|
| 3,553,975 | 11/1985 | Su .................................................. | 8/507 |
| 3,856,919 | 12/1979 | Rankin ............................................ | 424/80 |
| 3,947,573 | 3/1976 | Rankin ............................................ | 424/80 |
| 4,468,229 | 8/1984 | Su .................................................. | 351/162 |
| 4,559,059 | 12/1985 | Su .................................................. | 8/507 |
| 4,636,212 | 1/1987 | Posin et al. ..................................... | 351/162 |
| 4,713,375 | 12/1987 | Lindstrom et al. ............................. | 514/57 |

OTHER PUBLICATIONS

Finch, C. A., "Chemical Modification and Some Cross-Linking Reactions of Water Soluble Polymers" in *Chemistry and Technology of Water Soluble Polymers*, Plenum Press: New York, N.Y. (1983), pp. 92, 93, 95 and 108.

*Primary Examiner*—Ronald W. Griffin
*Attorney, Agent, or Firm*—Fliesler, Dubb, Meyer & Lovejoy

[57] ABSTRACT

This invention relates to a UV-blocked viscoelastic vitreous substitute for use in ophthalmic surgery comprising a hydroxy alkyl-substituted cellulose modified with a UV-absorbent molecule covalently bonded thereto having the type formula:

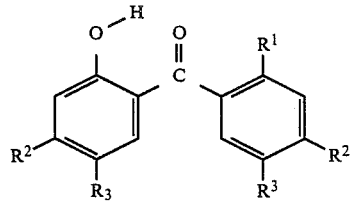

where $R^1$ is selected from the group consisting of H and OH; $R^2$ is selected from the group consisting of H, OH or OR where R is any alkyl group; and, $R^3$ is selected from the group consisting of H, $SO_3$, $OSO_2X$ where X is a leaving group.

5 Claims, 1 Drawing Sheet

VISCOELASTIC VITREOUS SUBSTITUTE WITH UV BLOCKER

BACKGROUND OF THE INVENTION

Phototoxic burns to macula of the eye have been observed by a number of experienced ophthalmic surgeons. These burns are induced by the ultraviolet light produced by the operating microscopes, particularly in extended surgical procedures lasting several hours which are not uncommon. "Maculopathy" as this problem is known in medical circles is receiving wider attention all the time. A number of articles have been written on the damaging effects of light on the retina of the of the eye, a few of which are listed below:

1. Ham, W. T., "Ocular Hazards of Light Sources: Review of Current Knowledge." J. Occupational Medicine, 25(2), 101–103,1983
2. Ham, W. T., Mueller, H. A., and Sliney, D. H., "Renal Sensitivity to Damage from Short Wavelength Light." Nature, 260,153–155,1976
3. Zigman, S., "Effects of Near Ultraviolet Radiation on the Lens and Retina." Docum, Ophthalmol 1983,55:375–391.
4. Werner, J. S., Hardenberg, F. E. "Spectral Sensitivity of the Pseudophakic Eye." Arch. Ophthalmol 1983,101:758–760
5. Mainster, M. A., "Spectral Transmission of Intraocular Lenses and Retinal Damage from Intense Light Sources." J. Am. J. Ophthalmol. 85,167–170,1978.

FIELD OF THE INVENTION

This invention relates to a unique ultraviolet (UV) blocker for use in combination with a viscoelastic material for direct insertion into the eye during ophthalmic surgery to protect the macula from radiation in the UV range.

DESCRIPTION OF THE RELATED ART

The prior art attempts at solving this problem have taken the form of an opaque silicone shield. The shield is placed on the cornea following intraocular lens implantation and is displaced while the wound is being sutured or the anterior chamber irrigated. There are, of course, several manufacturers of intraocular lenses containing a UV-absorbing compound bound chemically to the polymer matrix of the lens material; however, these lenses have nothing to do with opthalmic surgery.

The only other mechanism known to applicant for blocking the UV light reaching the eye during surgery is a simple UV filter through which the light from the operating microscope must pass before reaching the patients' eye. It appears, however, that the aforementioned prior art UV protective devices are not used as frequently as they should be because they are inconvenient and interfere with the surgical procedure being performed.

SUMMARY OF THE INVENTION

The invention comprises a hydroxy-substituted cellulose derivative used as a base but which has been modified by the addition of a benzophenoen analog thus converting a viscoelastic material having virtually no ability to absorb light in the ultraviolet range into one possessing superior UV blocking properties.

It is, therefore, the principal object of the present invention to provide a solution for use in the eye during ophthalmic surgery which protects the macula thereof from the harmful effects of ultraviolet light.

A second objective of the invention herein disclosed and claimed is that of providing a solution that can be inserted directly into the eye. Another object it to provide a UV blocker that can be chemically bonded to various hydroxy-substituted cellulose derivatives already proven non-toxic and effective vitreous substitutes.

An additional objective is to provide a formulation of the class described which demonstrates substantially complete absorbance in the 400 nanometer (nm) range while the hydroxy-substituted cellulose base alone shows only slight absorbance in the 220 nm area.

Further objects are to provide an ophthalmic solution which is clear and does not interfere with the operating or suturing procedures, possesses viscoelastic properties comparable to sodium hyaluronate in addition to its UV blocking capabilities, and one that is far less expensive and easier to use than the prior art filters and lenses.

Other objects will be in part apparent and in part pointed out specifically hereinafter in connection with the detailed description of the invention which follows the brief description of the two drawing figures that demonstrate in graphical form the transformation of the hydroxy-substituted cellulose base material having essentially no UV blocking capabilities into a very effective one through the addition of a very small percentage of a benzophenone analog.

Figure 2:
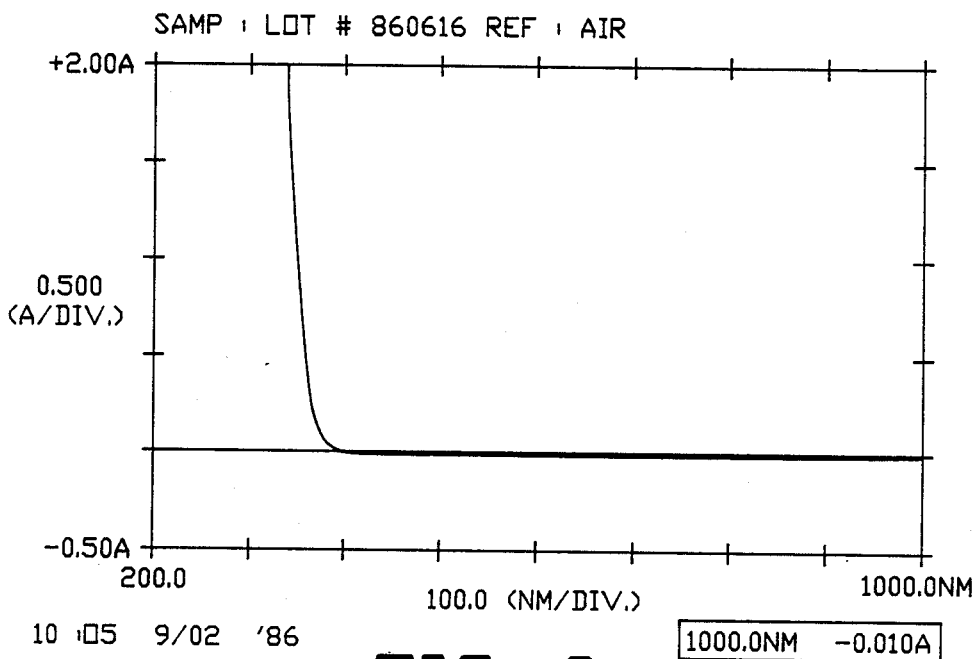

FIG. 1 is a graph showing the lack of any meaningful UV blocking capability of hydroxypropylmethyl cellulose; and, FIG. 2 is a comparable graph showing the same base with a benzophenone analog added which demonstrates complete UV absorbance in the 400 nm range.

In my copending U.S. application Ser. No. 07/045,326 filed May 4, 1987, now abandoned, I disclosed a viscoelastic composition for use as a vitreous substitute comprising a mixture of hydroxypropylmethyl cellulose and polyethylene oxide in a physiologic salt solution that is equal to if not superior to sodium hyaluronate for use in opthalmic surgery and as a topical solution to irrigate and lubricate the corneal tissues. This composition along with other hydroxy-substituted cellulose derivatives possess no meaningful ability to absorb radiation in the ultraviolet range, yet, as already noted, the operating microscope and other diagnostic light sources are capable of damaging the delicate macula of the eye. It has now been found in accordance with the teaching of the instant invention that this UV absorbing capability can be added to such compositions without detracting in any way from their viscoelastic properties by the simple, yet unobvious, expedient of chemically bonding thereto a benzophenone analog in accordance with the following reaction:

cellulose-OH +

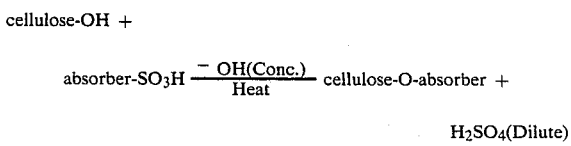

$H_2SO_4$(Dilute)

The product is based on hydroxy alkyl-substituted cellulose modified with an absorbing molecule which I now have discovered can be selected from either the benzophenone or triazole family. The absorbing species must, however, include at least one reactive functional group such as, for example, a carboxylic or sulphonic acid or acid chloride. Essentially, the chemistry is one of covalently binding a dye molecule to a cellulose fiber in the manner of chemically reactive dyes developed many years ago. U.S. Pat. No. 4,468,229 teaches the use of this same chemistry in the tinting of soft contact lenses. Cellulose in the aforementioned reaction functions as a polyalcohol, therefore, any group which can react with the alcoholic hydroxy groups to form a covalent bond will very likely react with cellulose.

In the reaction outlined above, the cellulose is reacted with the UV absorber under alkali conditions and elevated temperatures. By so doing, these conditions cause the trans-esterification reaction to be driven to the right thus resulting in the desired product. The actual reactive sites and species have not yet been clearly identified or isolated, however, the yield of UV-absorbing product remains quite high despite a number of side reactions taking place. Organic solvent extractions of an aqueous solution containing the reaction product using methyl-isobutyl ketone (MIBK) indicate almost complete conversion to the cellulose-abosrber complex. Specifically, a triple extraction followed by comparison of the (lambda max's) of the ketone extract and aqueous phase with the (lambda max's) of the MIBK and the absorber 2-hydroxy-4-methoxy-benzophenone-5 sulfonic acid (HMBPSA) confirm the absence of the absorber in either the MIBK or the aqueous phase. HMBPSA is soluble in MIBK as well as in water and should, therefore, be extractable into MIBK by using relatively larger volumes of the latter chemical to water during the extraction steps. The organic extract (lambda max) is identical to that of the MIBK, namely 336 mm. Comparison of the (lambda max) of the aqueous phase after extraction to the (lambda max) for HMBPSA shows the presence of a new chromophase (369.5 mm) which, upon the addition of small amounts of NaOH, shifted to 421.0 mm. This would be of a phenolic or hydroxyquinnone chromophore which would be present in the covalently-bound product.

Extraction of the reaction product with water and MIK converted the yellow reaction product in basic salt solution into a colorless basic salt solution. This would be consistent with the acidification of a neutral or basic salt solution product mixture. This acidification occurs by the dilution of the reaction product in basic salt solution with distilled water which has absorbed $CO_2$ prior to the MIBK extraction.

Due to substantial opportunity for the benzophenone and triazole-based absorbers to undergo hydrogen bonding, mixing them with hydroxy-substituted celluloses form relatively stable, UV-absorbing compounds. Examples of UV blockers effective in the 400 nm range are as follows:

EXAMPLE 1

A mixture of 497.5 g of distilled water, 2.0 g of hydroxypropylmethyl cellulose and 0.5 g of 2,2',4,4'-tetrahydroxy benzophenone formed a composition that absorbed 100% of the light below 400 nm in a 1 cm cell. The THBP in Example 1 above is associated with the HPMC through hydrogen-bonding.

EXAMPLE 2

A mixture of 250.0 g of distilled water, 2.0 g of hydroxpropylmethyl cellulose, 1.0 g of 2-hydroxy-4-methoxy-benzophenone-5 sulfonic acid and 0.15 g of NaOH was heated to 95° C. for two hours. This base material was then diluted with distilled water, plasticizers added and the pH adjusted using HCl to yield an effective UV-absorbing compound. Subsequent extraction with methyl-isobutyl ketone showed no unassociated 2-hydroxy-4-methoxy-benzophenone-5 sulfonic acid.

Finally, with brief reference to the drawings, FIG. 1 shows the absorbance spectrum of the unmodified base material consisting of 2% hydroxypropylmethyl cellulose. It reveals a very minor absorbance in the 220 nm range. In FIG. 2, on the other hand, where the base material was modified to include 0.2% of a benzophenone analog, specifically 2,2',4,4'-tetrahydroxy-benxophenone (THBP) from Example 1 above, the material thus modified demonstrated complete absorbance in the 400 nm range.

Both THBP and HMPPSA were analyzed using a Shimadzu UV-160 UV-Visible Recording Spectrophotometer. The samples were placed into a 1 mm path length quartz cell and analyzed through the entire working range of the instrument which is 1000 nm to 200 nm.

What is claimed is:

1. The viscoelastic vitreous substitute for blocking ultraviolet light during ophthalmic surgery which comprises: approximately 2% of a hydroxy-substituted cellulose derivative in a physiologic balanced salt solution convalently bonded to approximately 0.2% of a UV-absorbant molecule having the formula:

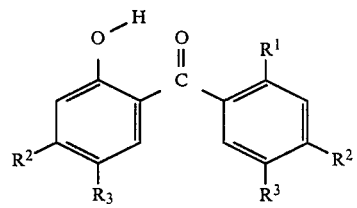

where $R^1$ is selected from the group consisting of H and OH; $R^2$ is selected from the group consisting of H, OH and OR where R is any alkyl group; and, $R^3$ is selected from the group consisting of H, $SO_3$, $OSO_2X$ and where X is selected from the group consisting of the alkali metals, the alkaline earth metals, hydroxyl, alkoxy and hydroxy groups.

2. The UV-blocked viscoelastic composition as set forth in claim 1 wherein: the hydroxy-substituted cellulose derivative comprises hydroxypropylmethyl cellulose.

3. The UV-blocked viscoelastic composition as set forth in claim 1 wherein: the UV absorbant molecule comprises 2-hydroxy-4-methoxy-benzophenone-5 sulfonic acid.

4. The UV-blocked viscoelastic composition as set forth in claim 1 wherein the hydroxy-substituted cellulose derivative is selected from the group consisting of hydroxymethyl cellulose, hydroxyethyl cellulose, hydroxyethylmethyl cellulose and carboxymethyl cellulose.

5. The viscoelastic vitreous substitute for blocking ultraviolet light during ophthalmic surgery which comprises: approximately 2% of a hydroxy-substituted cellulose derivative in a physiologic balanced salt solution covalently and hydrogen bonded to approximately 0.2% of a UV-absorbent molecule having the formula:

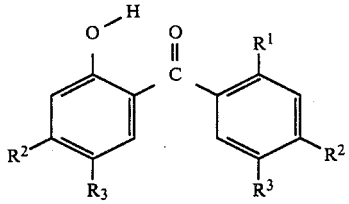

where $R^1$ is selected from the group consisting of H and OH; $R^2$ is selected from the group consisting of H, OH and OR where R is any alkyl group; and, $R^3$ is selected from the group consisting of H, $SO_3$, $OSO_2X$ and where X is selected from the group consisting of the alkali metals, the alkaline earth metals, hydroxyl, alkoxy and hydroxy groups.

* * * * *

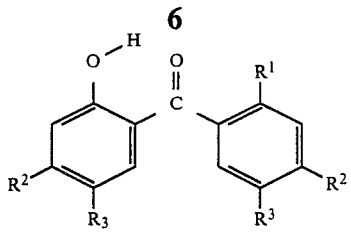

where $R^1$ is selected from the group consisting of H and OH; $R^2$ is selected from the group consisting of H, OH and OR where R is any alkyl group; and, $R^3$ is selected from the group consisting of H, $SO_3$, $OSO_2X$ and where X is selected from the group consisting of the alkali metals, the alkaline earth metals, hydroxyl, alkoxy and hydroxy groups.

* * * * *